United States Patent [19]

Ashitaka et al.

[11] Patent Number: 4,684,718

[45] Date of Patent: Aug. 4, 1987

[54] PROCESS FOR THE PREPARATION OF DIAZOCYANO ACIDS BY REACTING KETO-ACIDS WITH CYANOGEN COMPOUNDS

[75] Inventors: Hidetomo Ashitaka, Ichihara; Kazuya Jinda, Kisarazu; Yoshiyuki Miwa, Ichihara, all of Japan

[73] Assignee: UBE Industries, Ltd., Japan

[21] Appl. No.: 676,265

[22] Filed: Nov. 29, 1984

[30] Foreign Application Priority Data

Dec. 8, 1983 [JP] Japan .............................. 58-230640
Dec. 13, 1983 [JP] Japan .............................. 58-233669
Apr. 20, 1984 [JP] Japan .............................. 59-078385
Apr. 20, 1984 [JP] Japan .............................. 59-078386
Apr. 20, 1984 [JP] Japan .............................. 59-078387
Jun. 8, 1984 [JP] Japan .............................. 59-116547

[51] Int. Cl.$^4$ ................. C07C 101/26; C07C 107/02; C08F 4/04; C08G 63/68
[52] U.S. Cl. .................................... 534/586; 526/219; 528/292; 534/587; 534/838; 534/886; 534/887
[58] Field of Search ............... 534/586, 587, 838, 886, 534/887

[56] References Cited

U.S. PATENT DOCUMENTS

| | | | |
|---|---|---|---|
| 2,520,338 | 8/1950 | Robertson | 534/886 |
| 3,192,196 | 6/1965 | Vidal et al. | 534/886 X |
| 3,285,949 | 11/1966 | Siebert | 534/886 X |
| 3,775,395 | 11/1973 | Koyanagi et al. | 534/886 X |
| 4,101,522 | 7/1978 | Sheppard et al. | 534/838 X |
| 4,272,435 | 6/1981 | Matsuda et al. | 534/587 |

FOREIGN PATENT DOCUMENTS

| | | | |
|---|---|---|---|
| 2437403 | 4/1980 | France | 534/886 |
| 226588 | 1/1969 | U.S.S.R. | 534/886 |

*Primary Examiner*—Floyd D. Higel
*Attorney, Agent, or Firm*—Finnegan, Henderson, Farabow, Garrett & Dunner

[57] ABSTRACT

A process for the preparation of a diazocyano acid, which comprises reacting a keto-acid or its sodium salt with a cyanogen compound such as sodium cyanide or hydrogen cyanide and a hydrazine in water to form a concentrated aqueous solution of a hydrazo compound, adding acetone and/water to the concentrated aqueous solution to form a solution of the hydrazo compounds, adding chlorine gas to the solution to oxidize the hydrazo compound and form a diazocyano acid, adding acetone to the obtained reaction mixture during or after the oxidation if necessary, and separating and recovering the supernatant layer of the acetone-water solution containing the diazocyano acid from the mixture.

22 Claims, No Drawings

PROCESS FOR THE PREPARATION OF DIAZOCYANO ACIDS BY REACTING KETO-ACIDS WITH CYANOGEN COMPOUNDS

BACKGROUND OF THE INVENTION (1) Technical Field

The invention relates to a process for preparing a diazocyano acid such as 4,4'-azobis-(4-cyanovaleric acid) using a keto-acid such as levulinic acid or a sodium salt of a keto-acid as the starting material.

(2) Background Information

Diazocyano acids have been used as an initiator for polymerization such as homopolymerization of acrylamide or 1,3-butadiene or copolymerization of 1,3-butadiene with acrylonitrile (see, e.g., Japanese Examined Pat. Publication (Kokoku) No. 43-28474 and Japanese Unexamined Pat. Publication (Kokai) Nos. 56-133305 and 57-198720).

As means for the preparation of diazocyano acids, there is known a process comprising reacting a keto-acid or its sodium salt with a cyanogen compound such as sodium cyanide or hydrogen cyanide and a hydrazine such as hydrazine hydrate in water to form a hydrazo compound, adding chlorine gas to the obtained solution to oxidize the hydrazo compound and form a diazocyano acid and filtering off the solid diazocyano acid from the obtained reaction mixture (see, also, Japanese Examined Pat. Publication (Kokoku) No. 43-28474 and Japanese Unexamined Pat. Publication (Kokai) No. 56-133305).

However, this known process has the following problems:

(a) The yield of the diazocyano acid is low.

(b) Since sodium chloride is formed as a by-product in an amount of at least 2 moles per mole of a diazocyano acid when the diazocyano acid is synthesized, a large amount of sodium chloride is contained in the diazocyano acid product. A diazocyano acid containing a large amount of sodium chloride is not preferred as the initiator for homopolymerization of 1,3-butadiene or copolymerization of 1,3-butadiene with acrylonitrile.

(c) If a refining step is arranged for removing sodium chloride contained in the diazocyano acid, the yield of the diazocyano acid is drastically reduced.

SUMMARY OF THE INVENTION

The inventors conducted extensive research with a view to developing a novel process for the preparation of diazocyano acids in which the above-mentioned problems are overcome, and as the result, we have completed the present invention.

More specifically, in accordance with the present invention, there is provided a process for the preparation of a diazocyano acid, which comprises reacting a keto-acid or its sodium salt with a cyanogen compound such as sodium cyanide or hydrogen cyanide and a hydrazine in water to form a concentrated aqueous solution of a hydrazo compound, adding acetone and/or water to the concentrated aqueous solution to form a solution of the hydrazo compound, adding chlorine gas to the solution to oxidize the hydrazo compound and form a diazocyano acid, and separating the diazocyano acid from the obtained reaction mixture.

According to the present invention, diazocyano acids can be prepared in a high yield.

Furthermore, according to the present invention, large crystalline particles of sodium chloride are formed in the mixture of acetone and water by adjusting the ratio of acetone to water in the resulting reaction mixture within a specific range, preferably from 85/15 to 98/2, especially from 90/10 to 95/5, and thus, sodium chloride can be separated from the acetone-water mixture containing the diazocyano acid by a simple separation technique. Therefore, the process of the present invention is industrially advantageous.

DESCRIPTION OF THE PREFERRED EMBODIMENTS

In the process of the present invention, it is preferred that a keto-acid or its sodium salt (1 mole) be reacted with a cyanogen compound (0.95 to 1.5 moles, more preferably 1 mole) and a hydrazine (0.45 to 0.6 mole, more preferably 0.5 mole) in the presence or absence of a mineral acid such as hydrochloric acid or an alkali such as sodium hydroxide in a small amount of water, and a concentrated aqueous solution of a hydrazo compound may be obtained according to any of the following processes.

The aqueous solution of the hydrazo compound may be in a slurry state or in a transparent liquid state.

(a) The hydrazo compound is formed by reacting a keto-acid or its sodium salt with a mixture of the cyanogen compound such as sodium cyanide or hydrogen cyanide and the hydrazine. This reaction is carried out, preferably at a temperature of not higher than 50° C., especially 15° to 40° C., in the presence of water in an amount of 10 to 200 parts, especially 15 to 100 parts by weight per 100 parts by weight of the keto-acid or its sodium salt.

(b) The hydrazo compound is formed by contacting a keto-acid or its sodium salt with the cyanogen compound such as sodium cyanide or hydrogen cyanide and contacting the reaction product with the hydrazine. The reaction is carried out, preferably at a temperature of not higher than 50° C., especially not higher than 20° C., in the presence of water in an amount of 80 to 200 parts by weight per 100 parts by weight of the keto-acid or its sodium salt.

(c) A keto-acid or its sodium salt is reacted with the hydrazine in water preferably in an amount of 50 to 200 parts by weight per 100 parts by weight of the keto-acid or its sodium salt to form a ketazine, and the ketazine is reacted with the cyanogen compound such as hydrogen cyanide or sodium cyanide to form a concentrated aqueous solution of the hydrazo compound. Preferably, the reaction temperature is not higher than 100° C., especially 5° to 35° C.

It is preferred that, in the formation of the hydrazo compound by each process (a) to (c) as mentioned above, the pH value of the reaction system is adjusted to 5 to 9, especially 5.5 to 7.3 after the addition of the respective reactants. The pH value may be adjusted in a usual manner, for example, by addition of an aqueous NaOH or HCl.

Where a concentrated aqueous solution of the hydrazo compound is not employed, the yield of the diazocyano acid may be low.

As a preferred example of the keto-acid, there can be mentioned levulinic acid.

As a preferred example of the diazocyano acid, there can be mentioned 4,4'-azobis-(4-cyanovaleric acid).

As examples of the hydrazine, there can be mentioned hydrazine hydrate.

According to the process of the present invention, there may be obtained, for example, a concentrated aqueous solution of the reaction product, that is, a hydrazo compound of the following formula, at the above-mentioned step:

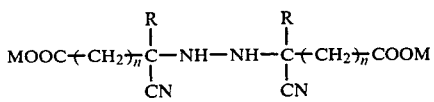

wherein R stands for alkyl of 1 to 6 carbon atoms, M stands for Na or H, and n is an integer of 1 to 6.

In the present invention, acetone, water or an acetone-water mixed solvent is added to the above-mentioned concentrated aqueous solution to form a solution of the hydrazo compound. It is preferred that acetone is added in an amount of not less than 100 parts by volume per 100 parts by volume of the concentrated aqueous solution. Especially, the acetone/water volume ratio is preferably from 85/15 to 98/2, more preferably from 90/10 to 95/5. In order to restrain the formation of azobisisobutyronitrile, acetone, water or the acetone-water mixed solvent is cooled below 10° C. before the addition.

Where an unreacted cyanogen compound or hydrazine may be retained in the above-mentioned concentrated aqueous solution, it is preferred that chlorine gas is added to the solution, before the addition of acetone, and after the addition of water as required, to react it with the unreacted compound, and thereafter, acetone or acetone and water are added and then chlorine gas is added to oxidize the hydrazo compound.

In the process of the present invention, chlorine gas is added to the above solution preferably in an amount of at least 0.5 mole, especially 0.5 to 0.75 mole, per mole of the keto-acid or its sodium salt to oxidize the hydrazo compound and form the diazocyano acid. It is preferred that this oxidation reaction be carried out at a temperature lower than 30° C., especially lower than 15° C.

Addition of chlorine gas can be performed according to known procedures at the above-mentioned oxidizing step.

In the process of the present invention, where acetone is not contained in the so-obtained reaction mixture, the non-soluble diazocyano acid is separated and recovered from the reaction mixture. NaCl is dissolved in water. In this case, the reaction mixture is preferably maintained at a temperature of not higher than 30° C., especially not higher than 10° C.

Where acetone is contained in the so-obtained reaction mixture, the acetone/water volume ratio in the reaction mixture containing the diazocyano acid is preferably adjusted to from 85/15 to 98/2, especially from 90/10 to 95/5, if necessary by adding water or acetone to the reaction mixture. The upper layer of the acetone-water solution containing the diazocyano acid is separated and recovered preferably at a temperature of 0° to 60° C., especially 0° to 45° C.

In the process of the present invention, when the diazocyano acid is formed by the above-mentioned oxidation reaction, sodium chloride is formed as a by-product in an amount of at least 2 moles per mole of the diazocyano acid. In the process of the present invention, by adjusting the ratio of acetone to water in the reaction mixture, sodium chloride formed is crystallized and precipitated in the mixture so that a very small amount of sodium chloride is dissolved in the acetone-water solution containing the diazocyano acid. If the volume ratio of acetone to water in the acetone-water solution of the hydrazo compound is already in the range of from 85/15 to 98/2, it may not be necessary to add acetone to the solution.

In the process of the present invention, in the case where hydrochloric acid is contained in the reaction mixture, it is preferred that a weakly alkaline compound such as sodium hydroxide, sodium carbonate or sodium hydrogencarbonate be added to neutralize hydrochloric acid and adjust the pH value of the solution to 3 to 5.

If the ratio of acetone to water in the mixture is below a ratio of 85/15 when the diazocyano acid containing acetone-water solution is separated and recovered, the diazocyano acid-containing solution may contain an extremely large amount of sodium chloride and, thus, the resulting diazocyano acid may contain a large amount of chlorine and sodium. If the ratio of acetone to water in the mixture is above a ratio of 98/2, an extremely large amount of a solvent is needed to dissolve the diazocyano acid.

In the separation and recovery of the supernatant acetone-water solution containing the diazocyano acid from the mixture, the mixture may be filtered to recover the diazocyano acid-containing acetone-water solution as the filtrate or may be decanted to recover the solution as the supernatant solution. By these procedures, the crystalline sodium chloride is separated and removed.

In the process of the present invention, the diazocyano acid may be recovered by evaporating and removing acetone and water from the diazocyano acid containing acetone-water solution and adding a small amount of water to the residual solid to effect water washing, or preferably, there may be adopted a method in which acetone is evaporated, water is added to the residue and the diazocyano acid is recovered by filtration. It is preferred that water be added to the residue left after evaporation of acetone in an amount of 100 to 1000 parts by weight, especially 100 to 500 parts by weight, per 100 parts by weight of the diazocyano acid, and the solid diazocyano acid be separated and recovered preferably at a temperature lower than 30° C., especially lower than 10° C., particularly after mixing the liquid homogeneously. If necessary, the recovered diazocyano acid may be dried under reduced pressure to remove a small amount of water contained in the diazocyano acid crystal.

According to the process as mentioned above, a diazocyano acid having a low Na content, preferably lower than 500 ppm can be prepared in a high yield, and if water washing is repeated several times, the Na content can be greatly reduced.

The diazocyano acid obtained by the above-mentioned process of the present invention may be purified to further reduce the Na content by dissolving the resulting diazocyano acid in a mixed solution of acetone and water at a volume ratio of from 75/25 to 95/5, preferably 75/25 to 90/10, evaporating acetone from the solution and washing the residue with water. By this purification procedure, the Na content of the diazocyano acid can be reduced to a level of lower than 5 ppm. It is preferred that the diazocyano acid having an Na content lower than 3000 ppm, especially lower than 500 ppm, be dissolved in the above-mentioned acetone-water solution.

It is preferred that the amount of the diazocyano acid is 1 to 60 g, especially 5 to 30 g, per 100 ml of the acetone-water solution. It is also preferred that the diazocyano acid be dissolved in the acetone-water solution at a tmeperature lower than 50° C., especially lower than 40° C. Acetone is removed by evaporation from the acetone-water solution containing the diazocyano acid (it is not necessary to completely remove acetone at this step), and the diazocyano acid precipitated in the remaining aqueous solution is separated, recovered and washed with water. There is preferably adopted a process in-which water is added to the precipitated diazocyano acid in the aqueous solution to effect water washing and the diazocyano acid is recovered by filtration.

In the above-mentioned process, it is preferred that evaporation of acetone from the acetone-water solution containing the diazocyano acid be carried out at a temperature lower than 50° C., especially lower than 40° C. It also is preferred that acetone be evaporated until the acetone/water volume ratio is from 25/75 to 0/100, especially from 10/90 to 0/100, before filtration.

In the process, preferably, water is added to the residue left after the above-mentioned step of evaporation of acetone in an amount of 100 to 1500 parts by weight, especially 100 to 1000 parts by weight, per 100 parts by weight of the diazocyano acid, preferably followed by mixing, and the solid diazocyano acid is separated and recovered at a temperature lower than 10° C., preferably lower than 3° C. Separation and recovery of the diazocyano acid can be accomplished by known means.

It is preferred that the diazocyano acid separated and recovered at the above-mentioned step be washed with water in an amount of 50 to 400 parts by weight, especially 100 to 250 parts by weight, per 100 parts by weight of the diazocyano acid at a temperature lower than 10° C., especially lower than 3° C. If necessary, a small amount of water contained in the diazocyano acid may be removed by drying under reduced pressure.

According to the above-mentioned process, a diazocyano acid having an Na content lower than 5 ppm can be obtained at a recovery percentage higher than 90% based on the crude diazocyano acid, and if the above-mentioned procedures are repeated on the so-obtained diazocyano acid having the reduced Na content, further purified diazocyano acid can be obtained.

The diazocyano acid prepared according to the process of the present invention can be used as the initiator for polymerization such as homopolymerization of 1,3-butadinene or copolymerization of 1,3-butadiene with acrylonitrile. Further, the diazocyano acid-containing acetone-water solution formed as the supernatant layer according to the process of the present invention can be used as the initiator solution without isolating the diazocyano acid.

It is preferred that the polymerization temperature be 70° to 130° C. and the polymerization time be 1 to 40 hours. It is preferred that the amount of the diazocyanoacid be 5 to 20 parts by weight per 100 parts by weight of the monomer component (1,3-butadiene or the sum of 1,3-butadiene and acrylonitrile). The method for the addition of the diazocyano acid or the acetone-water solution containing the diazocyano acid is not particularly critical. The solution may be added intermittently or continuously. It is preferred that a carboxyl-terminated liquid polymer having an acrylonitrile content of up to 45% by weight, especially 15 to 35% by weight, a number average molecular weight of 1000 to 5000 and a functional group number of 1.8 to 2.5 per mole be formed by appropriately adjusting the polymerization conditions.

The so-separated liquid polymer may be mixed with an antioxidant according to a known method.

Unreacted 1,3-butadiene is removed from the polymerization reaction mixture if necessary, and water is added to the polymerization reacton mixture to wash the liquid polymer and the liquid polymer is separated and recovered. It is preferred that the liquid polymer be dried in an evaporator until the weight is not changed any more. Thus, the intended carboxyl-terminated polymer is obtained.

It is preferred that the amount of water added at this step be 100 to 400 parts by weight per 100 parts by weight of the carboxyl-terminated liquid polymer.

In the case where unreacted 1,3-butadiene is not removed from the polymerization reaction mixture, it is preferred that water be added so that the amount of acetone is 50 to 300 parts by weight, the amount of 1,3-butadiene is 10 to 100 parts by weight and the amount of water is 100 to 400 parts by weight per 100 parts by weight of the carboxyl-terminated liquid polymer. After the addition of water, mixing is preferably carried out to disperse the polymer, and when the mixture is allowed to stand still, preferably for 2 minutes to 10 hours, the mixture is separated into the phase of the liquid polymer-acetone solution and the phase of the acetone-water solution. The liquid polymer is separated and recovered from this mixture. If necessary, a small amount of water contained in the liquid polymer may be removed by centrifugal separation.

In the process of the present invention, by separating the liquid polymer from the acetone-water solution, water-soluble compounds formed as by-products at the step of preparing the diazocyanoacid are removed in the dissolved state in the acetone-water solution. Furthermore, substantially all of a small amount of sodium chloride contained in the acetone-water solution of the diazocyanoacid used as the polymerization initiator is removed from the liquid polymer.

The liquid polymer is dried in an evaporator until the weight is not changed any more.

As the evaporator, there may be used centrifugal film evaporators such as a lateral centrifugal film evaporator, a vertical centrifugal film evaporator and a VL-type centrifugal film evaporator.

The carboxyl-terminated liquid polymer prepared according to the process of the present invention can be used for the production of electro-deposition paints and powder paints and IC packaging materials.

The present invention will now be described in detail with reference to the following examples and comparative examples. In the examples, the pH of the reaction mixture was adjusted to 4 after the addition of all the three reaction components.

EXAMPLE 1

A reaction vessel equipped with a stirrer, a gas-introducing pipe, a gas vent and a dropping pipe was charged with 0.963 kg (8.3 mole) of levulinic acid and 0.42 1 of water, and the mixture was cooled to 5° C. After addition of 0.058 kg of concentrated hydrochloric acid and 0.08 1 of water, a solution of 0.420 kg (8.5 mole) of NaCN in 0.83 1 of water was added dropwise to the mixture while cooling the mixture so that the reaction temperature did not exceed 10° C., and thereafter, the mixture was left to react at a temperature not higher than 10° C. for 15 minutes. The cyanhydrin thus formed was precipitated and the mixture became like a soft ice cream. To the mixture 0.208 kg (4.15 mole) of $NH_2NH_2.H_2O$ was added dropwise, and the mixture was warmed to 30° C. to form a liquid, and then the liquid was left to react at 35° C. for 3 hours. The mixture was then cooled to 5° C., added with 12 l of acetone and then with 0.315 kg (4.5 mole) of $Cl_2$ gas, and left to react while keeping the temperature below 10° C. After the completion of reaction, the temperature of the mixture was raised to 20° C. and the stirring was stopped. Thus, the mixture was clearly separated into a faintly yellow liquid portion and a white precipitate portion. The liquid portion was acidic due to hydrochloric acid and, thus, the mixture was adjusted to a pH of 3.5 with the addition of $NaHCO_3$. Then, the white precipitate portion was filtered off, and the liquid portion was maintained at 20° C. and acetone was removed by distillation using an aspirator to precipitate a large amount of 4,4'-azobis(4-cyanovaleric acid) (hereinafter referred to as ACVA). The residual mixture was added 2 l of water, cooled to 5° C. and washed while stirring at this temperature, and ACVA was recovered by suction filtration. The recovered ACVA was dried under reduced pressure at 20° C. until the weight was not changed, whereby 0.835 kg of pure-white ACVA was obtained. One peak was observed by the liquid chlomatography. The results of the elementary analysis of ACVA ($C_{12}H_{16}N_4O_4$) were as follows:
Calculated Values C=51.43%, H=5.75%, N=19.99% Found Values C=51.52%, H=5.68%, N=19.85%

The NaCl content in ACVA was 62 ppm.

EXAMPLE 2

A reaction vessel equipped with a stirrer, a gas-introducing pipe, a gas vent and a dropping pipe was charged with 0.963 kg (8.3 mole) of levulinic acid and 0.42 l of water, and the mixture was cooled to 5° C. After addition of 0.058 kg of concentrated hydrochloric acid and 0.08 l of water, a solution of 0.420 kg (8.5 mole) of NaCN in 0.83 l of water was added dropwise to the mixture while cooling the mixture so that the reaction temperature did not exceed 10° C., and thereafter, the mixture was left to react at a temperature not higher than 10° C. for 15 minutes. The cyanhydrin thus formed was precipitated and the mixture became like a soft ice cream. To the mixture 0.208 kg (4.15 mole) of $NH_2NH_2.H_2O$ was added dropwise, and the mixture was warmed to 30° C. to form a liquid, and then the liquid was left to react at 35° C. for 3 hours. Water is distilled off under reduced pressure at this temperature, until the amount of water contained in the system becomes 0.63 l. The mixture was then cooled to 5° C., added with 12 l of acetone and then with 0.315 kg (4.5 mole) of $Cl_2$ gas, and left to react while keeping the temperature below 10° C. After completion of the reaction, the temperature of the mixture was raised to 20° C. and the stirring was stopped. Thus, the mixture was clearly separated into a faintly yellow liquid portion and a white precipitate portion. The liquid portion was acidic due to hydrochloric acid and, thus, the mixture was adjusted to a pH of 3.5 with the addition of $NaHCO_3$. Then, the white precipitate portion was filtered off, and the liquid portion was maintained at 20° C. and acetone was removed by distillation using an aspirator to precipitate a large amount of ACVA. The residual mixture was added 2.7 l of water, cooled to 5° C. and washed while stirring at this temperature, and ACVA was recovered by suction filtration. The recovered ACVA was dried under reduced pressure at 20° C. until the weight was not changed, whereby 0.835 kg of pure-white ACVA. One peak was observed by the liquid chlomatography. The results of the elementary analysis of ACVA ($C_{12}H_{16}N_4O_4$) were as follows:
Calculated Values C=51.43%, H=5.75%, N=19.99% Found Values C=51.35%, H=5.79%, N=20.21%

The NaCl content in ACVA was 28 ppm.

Comparative Example 1

A reaction vessel equipped with a stirrer, a gas-introducing pipe, a gas vent and a dropping pipe was charged with 0.963 kg (8.3 mole) of levulinic acid and 1.0 l of water, and the mixture was cooled to 5° C. After addition of 0.058 kg of concentrated hydrochloric acid and 0.3 l of water, a solution of 0.420 kg (8.5 mole) of NaCN in 1.6 l of water was added dropwise to the mixture while cooling the mixture so that the reaction temperature did not exceed 10° C., and thereafter, the mixture was left to react at a temperature not higher than 10° C. for 15 minutes. No product was precipitated, unlike in Example 1. To the mixture 0.208 kg (4.15 mole) of $NH_2NH_2.H_2O$ was added dropwise, and the mixture was left to react at 35° C. for 3 hours. The mixture was then cooled to 5° C., added with 3.3 l of acetone and then with 0.31 kg (4.4 mole) of $Cl_2$ gas, and left to react while keeping the temperature below 10° C. Acetone was removed by distillation under reduced pressure from the reaction mixture in which ACVA was partially precipitated to precipitate a large amount of ACVA. Crude ACVA was obtained by suction filtration over the period of 3 hours. The crude ACVA was washed with 0.7 l of water, filtered, and dried under reduced pressure to obtain 0.69 kg of ACVA. The NaCl content in ACVA was 2000 ppm.

EXAMPLE 3

A 1-liter 4-neck flask equipped with a stirrer, a gas-introducing pipe, a gas vent and a dropping pipe was charged with 25.25 g (0.53 mole) of NaCN, 15 ml of $H_2O$ and 12.52 g (0.25 mole) of $NH_2NH_2.H_2O$, and the mixture was stirred at 25° C. A part of NaCN was left granular even after stirring. Then, a liquid formed by adding 3.5 g of concentrated HCl to 58.0 g (0.5 mole) of levulinic acid was added dropwise to the mixture while maintaining the reaction temperature at 25° to 28° C. A faintly yellow, slightly viscous slurry was formed and the insoluble granules of NaCN disappeared during the dropwise addition. To the mixture 7 g of concentrated HCl was added, the temperature was elevated to 35° C. and reaction was carried out for 3 hours at this temperature. The mixture was kept in the slurry state. The mixture was cooled to 5° C., and 540 ml of acetone and 40 ml of $H_2O$ were added to the mixture. Then, 21.3 g (0.3 mole) of $Cl_2$ gas was blown into the mixture while cooling the mixture so that the reaction temperature did not exceed 10° C. After the completion of reaction, the temperature of the mixture was raised to 20° C. and the stirring was stopped. Thus, the mixture was clearly separated into a faintly yellow liquid portion and a white precipitate portion. Then, the white precipitate portion was filtered off, and the liquid portion was maintained at 20° C. and acetone was removed by distillation using an aspirator to precipitate a large amount of ACVA. The residual mixture was added 200 ml of water, cooled to 5° C. and washed while stirring at this temperature, and ACVA was recovered by suction filtration. The recovered ACVA was dried under reduced pressure at 20° C. until the weight was not changed, whereby 63.57 g of pure-white ACVA. One peak was observed by the liquid chlomatography. The yield was 90.7% based on levulinic acid. The results of the elementary analysis of ACVA ($C_{12}H_{16}N_4O_4$) were as follows:

Calculated Values C=51.43%, H=5.75%, N=19.99% Found Values C=51.29%, H=5.58%, N=20.05%

The Na content in ACVA was 180 ppm.

EXAMPLE 4

A 1-liter 4-neck flask equipped with a stirrer, a gas-introducing pipe, a gas vent and a dropping pipe was charged with 25.25 g (0.53 mole) of NaCN, 15 ml of $H_2O$ and 12.52 g (0.25 mole) of $NH_2NH_2.H_2O$, and the mixture was stirred at 25° C. A part of NaCN was left granular even after stirring. Then, a liquid formed by adding 3.5 g of concentrated HCl to 58.0 g (0.5 mole) of levulinic acid was added dropwise to the mixture while maintaining the reaction temperature at 25 to 28° C. A faintly yellow, slightly viscous slurry was formed and the insoluble granules of NaCN disappeared during the dropwise addition. The temperature was elevated to 35° C. and reaction was carried out for 3 hours at this temperature. The mixture was kept in the slurry state. The mixture was cooled to 5° C., and 540 ml of acetone and 40 ml of $H_2O$ were added to the mixture. Then, 21.3 g (0.3 mole) of $Cl_2$ gas was blown into the mixture while cooling the mixture so that the reaction temperature did not exceed 10° C. After the completion of reaction, the temperature of the mixture was raised to 20° C. and the stirring was stopped. Thus, the mixture was clearly separated into a faintly yellow liquid portion and a white precipitate portion. Then, the white precipitate portion was filtered off, and the liquid portion was maintained at 20° C. and acetone was removed by distillation using an aspirator to precipitate a large amount of ACVA. The residual mixture was added with 200 ml of water, cooled to 5° C. and washed while stirring at this temperature, and ACVA was recovered by suction filtration. The recovered ACVA was dried under reduced pressure at 20° C. until the weight was not changed, whereby 63.85 g of pure-white ACVA. One peak was observed by the liquid chromatography. The yield was 91.1% based on levulinic acid. The Na content in ACVA was 210 ppm.

EXAMPLE 5

A 1-liter 4-neck flask equipped with a stirrer, a gas-introducing pipe, a gas vent and a dropping pipe was charged with 25.25 g (0.53 mole) of NaCN, 50 ml of $H_2O$ and 12.52 g (0.25 mole) of $NH_2NH_2.H_2O$, and the mixture was stirred at 25° C. A part of NaCN was left granular even after stirring. Then, a liquid formed by adding 3.5 g of concentrated HCl to 58.0 g (0.5 mole) of levulinic acid was added dropwise to the mixture while maintaining the reaction temperature at 25° to 28° C. A faintly yellow, slightly viscous slurry was formed and the insoluble granules of NaCN disappeared during the dropwise addition. To the mixture 7 g of concentrated HCl was added, the temperature was elevated to 35° C. and reaction was carried out for 3 hours at this temperature. The mixture was kept in the slurry state. The mixture was cooled to 5° C., and 540 ml of acetone and 40 ml of $H_2O$ were added to the mixture. Then, 21.3 g (0.3 mole) of $Cl_2$ gas was blown into the mixture while cooling the mixture so that the reaction temperature did not exceed 10° C. After completion of the reaction, the temperature of the mixture was raised to 20° C. and the stirring was stopped. Thus, the mixture was clearly separated into a faintly yellow liquid portion and a white precipitate portion. Then, the white precipitate portion was filtered off, and the liquid portion was maintained at 20° C. and acetone was removed by distillation using an aspirator to precipitate a large amount of ACVA. The residual mixture was added 200 ml of water, cooled to 5° C. and washed while stirring at this temperature, and ACVA was recovered by suction filtration. The recovered ACVA was dried under reduced pressure at 20° C. until the weight was not changed, whereby 58.87 g of pure-white ACVA. One peak was observed by the liquid chlomatography. The yield was 84.0% based on levulinic acid. The Na content in ACVA was 230 ppm.

COMPARATIVE EXAMPLE 2

A 2-liter 4-neck flask equipped with a stirrer, a gas-introducing pipe, a gas vent and a dropping pipe was charged with 58.0 g (0.5 mole) of levulinic acid, 3.5 g of concentrated HCl and 130 ml of water, and the mixture was cooled to 5° C. A solution of 25.25 g (0.53 mole) of NaCN in 50 ml of water was added dropwise to the mixture while maintaining the temperature of the mixture at 5° C. The reaction mixture was colorless and transparent. To the mixture 12.52 g (0.25 mole) of $NH_2NH_2.H_2O$ was added dropwise, and the mixture was warmed to 35° C. and stirred for 3 hours. The mixture was then cooled to 5° C., added with 1000 ml of acetone and then with 21.3 g (0.3 mole) of $Cl_2$ gas while maintaining the temperature at 5° to 10° C. After the completion of reaction, the temperature of the mixture was raised to 20° C. and the stirring was stopped. Then, the mixture was treated and dried as mentioned in Example 3 to obtain 45.5 g of ACVA. The yield was 65% based on levulinic acid.

EXAMPLE 6

A 1-liter 4-neck flask equipped with a stirrer, a gas-introducing pipe, a gas vent and a dropping pipe was charged with 58.0 g (0.5 mole) of levulinic acid and 50 ml of water, and the mixture was cooled to 5° C. 12.52 g (0.25 mole) of $NH_2NH_2.H_2O$ was added dropwise while maintaining the temperature below 10° C. A colorless, viscous slurry was formed. Stirring was continued for about 15 minutes at a temperature below 10° C., and a solution of 25.25 g (0.53 mole) of NaCN in 50 ml of water was added dropwise to the mixture while cooling the mixture so that the reaction temperature did not exceed 10° C. During the addition, the mixture was changed to a faintly yellow liquid from the slurry state, and had a pH of 10 at the end of addition. The mixture was adjusted to a pH of 10 with the addition of 2.5 g of concentrated HCl. The mixture was then warmed to 20° C., and stirred at this temperature for 15 hours. The mixture was then cooled to 5° C., added with 700 ml of acetone and then with 21.3 g (0.3 mole) of $Cl_2$ gas, and left to react while maintaining the temperature below 10° C. After the completion of reaction, the temperature of the mixture was raised to 20° C. and the stirring was stopped. Thus, the mixture was clearly separated into a faintly yellow liquid portion and a white precipitate portion. Then, the white precipitate portion was filtered off, and the liquid portion was maintained at 20° C. and acetone was removed by distillation using an aspirator to precipitate a large amount of ACVA. The residual mixture was added 200 ml of water, cooled to 5° C. and washed while stirring at this temperature, and ACVA was recovered by suction filtration. The recovered ACVA was dried under reduced pressure at 20° C. until the weight was not changed, whereby 58.6 g (84%) of pure-white ACVA. The results of the elementary analysis of ACVA ($C_{12}H_{16}N_4O_4$) were as follows:

Calculated Values C=51.43%, H=5.75%, N=19.99% Found Values C=51.49%, H=5.78%, N=20.01%

The Na content in ACVA was 205 ppm.

EXAMPLE 7

The procedure as in Example 6 was repeated before the addition of acetone. The resulting mixture was then cooled to 5° C. and added with 200 ml of water and with 21.3 g of $Cl_2$ gas. Then, the formed pure-white ACVA was filtered off at 5° C. The obtained ACVA was washed with 100 ml of water at 5° C. and dried under reduced pressure until the weight became constant. The yield was 57.8 g and the Na content was 610 ppm.

EXAMPLE 8

A 1-liter 4-neck flask equipped with a stirrer, a gas-introducing pipe, a gas vent and a dropping pipe was charged with 25.25 g (0.53 mole) of NaCN, 15 ml of $H_2O$ and 12.52 g (0.25 mole) of $NH_2NH_2.H_2O$, and the mixture was stirred at 25° C. A part of NaCN was left granular even after stirring. Then, a liquid formed by adding 8.0 g of concentrated HCl to 58.0 g (0.5 mole) of levulinic acid was added dropwise to the mixture while maintaining the reaction temperature at 20° to 23° C. A faintly yellow, slightly viscous slurry was formed and the insoluble granules of NaCN disappeared during the dropwise addition. The temperature was elevated to 35° C. and reaction was carried out for 1 hour at this temperature. The mixture was kept in the slurry state. The mixture was cooled to 5° C., kept at 5° C. for 3.5 hours, and 560 ml of $H_2O$ was added to the mixture. Then, 21.3 g (0.3 mole) of $Cl_2$ gas was blown into the mixture while cooling the mixture so that the reaction temperature did not exceed 10° C. The mixture was added with 100 ml of $H_2O$, stirred at 3° C. for 30 minutes, and then filtered with G3 glass filter. Then, the mixture was washed with distilled water of below 3° C.

The mixture was then dried at room temperature on $P_2O_5$ under reduced pressure, and thus, 62.3 g of ACVA was obtained. The yield was 89% based on levulinic acid. The Na content was 590 ppm.

EXAMPLE 9

A flat bottom flask having a capacity of 1 liter was charged with 55 g of dried ACVA (having an Na content of 610 ppm and obtained as in Example 7), and 350 ml of an acetone-water mixed solvent (A/W by vol.=75/25) was added and ACVA was dissolved therein at a temperature lower than 40° C. Then, acetone was removed by distillation under reduced pressure at a temperature lower than 40° C., whereby ACVA was gradually precipitated in water. After acetone had been completely removed, 400 ml of distilled water was added to the solution having ACVA precipitated therein. The mixture was stirred under cooling to 1° to 3° C. for 30 minutes and suction filtration was carried out by using G4 glass filter, and the recovered solid was washed with 100 ml of distilled water (1° to 3° C.) two times and dried under reduced pressure in the presence of $P_2O_5$ to recover 51.7 g (94%) of ACVA having an Na content of 1.3 ppm as determined by the atomic absorption spectroscopy.

Then, a flat bottom flask having a capacity of 500 ml was charged with 40.0 g of the sample obtained above, and 250 ml of an acetone-water mixed solvent (A/W=75/25) was added and the sample was dissolved therein at a temperature lower than 40° C. When acetone was removed by distillation under reduced pressure, ACVA was gradually precipitated in water. After acetone had been completely removed, 100 ml of distilled water was added to the solution having ACVA precipitated therein and the mixture was stirred under cooling to 1° to 3° C. for 30 minutes. Suction filtration was performed by G4 glass filter and the solid was washed with 100 ml of distilled water (1° to 3° C.) two times and dried under reduced pressure in the presence of $P_2O_5$ to recover 37.2 g (93%) of ACVA having an Na content of 0.4 ppm as determined by the atomic absorption spectroscopy.

EXAMPLE 10

A 10-liter 4-neck flask equipped with a stirrer, a gas-introducing pipe, a gas vent and a dropping pipe was charged with 284.8 g (5.811 mole) of NaCN, 165 ml of $H_2O$ and 137.3 g (2.741 mole) of $NH_2NH_2.H_2O$, and the mixture was stirred at 25° C. A major of NaCN was left granular even after stirring. Then, a liquid formed by adding 54.8 g of concentrated HCl to 636.6 g (5.483 mole) of levulinic acid was added dropwise to the mixture while maintaining the reaction temperature at 20° to 22° C. A faintly yellow, slightly viscous slurry was formed and the insoluble granules of NaCN disappeared during the dropwise addition. To the mixture 54.8 g of concentrated HCl was added, the temperature was elevated to 35° C. and reaction was carried out for 1 hour at this temperature. The mixture was then cooled to 5° C. with ice water and left to stand for 2 hours. The mixture was kept in a white slurry state. The mixture was cooled to 3° C., 494 ml of water was added while again starting stirring, and 6372 ml of acetone of 4° C. was added to the mixture. Then, 233 g (3.29 mole) of $Cl_2$ gas was blown into the mixture while cooling the mixture so that the reaction temperature did not exceed 10° C. After completion of the reaction, the temperature of the mixture was raised to 20° C. and the stirring was stopped. Thus, the mixture was clearly separated into a faintly yellow liquid portion and a white precipitate portion. The liquid portion was acidic due to hydrochloric acid and, thus, the mixture was adjusted to a pH of 3.5 with the addition of $NaHCO_3$. Then, the white precipitate portion was filtered off to obtain a faintly yellow transparent liquid in an amount of 7434 ml. The liquid contained 708.0 g (2.526 mole) of ACVA. The yield was 92.16%, and the Na content was 500 ppm as measured by atomic-absorption spectroscopy.

This liquid was used as an initiator solution for polymerization. A 35 l autoclave equipped with a magnetic stirrer, a thermometer, a charge-injection pipe, a coiled condenser and a vent was charged with 5275 g of 1,3-butadiene, 1136 g of acrylonitrile and 755 g of acetone, and the mixture was heated to 85° C. At this temperature, 630 ml of the initiator solution which contained 60 g of ACVA was injected into the autoclave. Additional portions of ACVA and acrylonitrile were added every 30 minutes according to the following addition program.

| Hrs. from starting polymerization | Acrylonitrile (g) | ACVA (g) | Hrs. from starting polymerization | Acrylonitrile (g) | ACVA (g) |
| --- | --- | --- | --- | --- | --- |
| 0.5 | 34.5 | 39.3 | 9.5 | 19.2 | 15.0 |
| 1.0 | 33.9 | 36.3 | 10.0 | 18.6 | 14.4 |
| 1.5 | 32.4 | 34.2 | 10.5 | 17.7 | 13.8 |
| 2.0 | 31.2 | 32.1 | 11.0 | 17.4 | 13.5 |
| 2.5 | 30.3 | 30.3 | 11.5 | 16.8 | 12.9 |
| 3.0 | 29.1 | 28.5 | 12.0 | 16.2 | 12.6 |
| 3.5 | 28.2 | 26.7 | 12.5 | 15.6 | 12.3 |
| 4.0 | 27.3 | 25.2 | 13.0 | 15.3 | 12.0 |
| 4.5 | 26.4 | 24.0 | 13.5 | 14.7 | 11.7 |
| 5.0 | 25.5 | 22.5 | 14.0 | 14.1 | 11.4 |
| 5.5 | 24.6 | 21.6 | 14.5 | 13.8 | 11.1 |
| 6.0 | 24.0 | 20.4 | 15.0 | 13.2 | 10.8 |
| 6.5 | 23.1 | 19.5 | 15.5 | 12.9 | 10.5 |
| 7.0 | 22.2 | 18.6 | 16.0 | 12.6 | 10.5 |
| 7.5 | 21.6 | 17.7 | 16.5 | 12.0 | 10.2 |
| 8.0 | 21.0 | 16.8 | 17.0 | 11.7 | 9.9 |
| 8.5 | 20.4 | 16.2 | 17.5 | 11.1 | 9.9 |
| 9.0 | 19.5 | 15.6 | | | |

The polymerization time was 18 hours, and the polymerization temperature was maintained at 85° C.±0.2° C. except for the temperature drops within 1° C. for about 2 minutes at the time of the addition of the acrylonitrile and ACVA.

After the polymerization for 18 hours, ice water was introduced into the coiled condenser and the autoclave was dipped into ice water to rapidly cool the reaction mixture and stop the polymerization. 20000 g of water was added to 14200 g of the polymerization liquid, and the mixture was stirred and then left to stand. Thus, the mixture was rapidly separated into two layers. The lower water-acetone layer was removed, and the upper polymer layer was added with 5000 g of acetone to dissolve the polymer. Then, 8500 g of water was added, and the mixture was stirred and then left to stand. After the separation of the mixture into two layers, the lower layer was removed and the upper polymer layer was dried in a centrifugal film evaporator until the weight was not changed any more, whereby 6300 g of a carboxyl-terminated liquid polymer was obtained. The monomer conversion was 82%.

This liquid copolymer had an acrylonitrile content of 24.8 mole %, an acid value of 1850 g/eq, and an Na content of 12.0 ppm as measured by atomic-absorption spectroscopy. The ratio of the molecular-weight distribution indices Mw/Mn was 1.96.

EXAMPLE 11

750 g of ACVA having an Na content of 28 ppm and obtained as in Example 2 was dissolved in 7.5 l of an acetone-water (acetone/water=9/1) mixture. Using 7.88 l of the solution of ACVA in acetone-water as an initiator solution, the polymerization procedure as in Example 10 was repeated, and the resultant polymer was washed with water and dried.

Thus, 6380 g of a carboxyl-terminated butadieneacrylonitrile copolymer was obtained. This copolymer had an acrylonitrile content of 24.6%, an acid value of 1870 g/eq, and an Na content of 0.7 ppm as measured by atomic-absorption spectroscopy.

We claim:

1. A process for the preparation of diazocyano acid, which comprises reacting a keto-acid with sodium cyanide and a hydrazine or reacting a sodium salt of a keto-acid with hydrogen cyanide and a hydrazine in the presence of water in an amount of not more than 200 parts by weight of water per 100 parts by weight of the keto-acid or its sodium salt to form a concentrated aqueous solution of a hydrazo compound, adding acetone or acetone and water to the concentrated aqueous solution to form a solution of the hydrazo compound so that a volume ratio of 85/15 to 98/2 of acetone to water in a reaction mixture containing a diazocyano acid and resulting from the next oxidation step is attained, adding chlorine gas to the solution to oxidize the hydrazo compound and form the diazocyano acid, and separating the supernatant acetone-water solution containing the diazocyano acid and recovering the diazocyano acid from the acetone-water solution.

2. A process according to claim 1, wherein the volume ratio is in the range of from 90/10 to 95/5.

3. A process according to claim 1, wherein 1 mole of the keto-acid or its sodium salt is reacted with 0.95 to 1.5 moles of the cyanogen compound and 0.45 to 0.6 mole of the hydrazine.

4. A process according to claim 1, wherein the concentrated aqueous solution of the hydrazo compound is formed by reacting the keto-acid or its sodium salt with a mixture of the cyanogen compound and the hydrazine in water.

5. A process according to claim 4, wherein the amount of water is 10 to 200 parts by weight per 100 parts by weight of the keto-acid or its sodium salt.

6. A process according to claim 1, wherein the concentrated aqueous solution of the hydrazo compound is formed by reacting the keto-acid or its sodium salt with the cyanogen compound in water to form cyanohydrin and reacting the cyanohydrin with the hydrazine.

7. A process according to claim 6, wherein the reaction of the keto-acid or its sodium salt with the cyanogen compound is carried out at a temperature lower than 20° C.

8. A process according to claim 6, wherein the amount of water is 80 to 200 parts by weight per 100 parts by weight of the keto-acid or its sodium salt.

9. A process according to claim 1, wherein the concentrated aqueous solution of the hydrazo compound is formed by reacting the keto-acid or its sodium salt with the hydrazine in water to form a ketazine and reacting the ketazine with the cyanogen compound.

10. A process according to claim 9, wherein the amount of water is 50 to 200 parts by weight per 100 parts by weight of the keto-acid or its sodium salt.

11. A process according to claim 1, wherein a small amount of chlorine gas is added to the concentrated aqueous solution of the hydrazo compound, after the addition of water as required, acetone is added to form an acetone-water solution containing the hydrazo compound, and then chlorine gas is added to oxidize the hydrazo compound.

12. A process according to claim 1, wherein the hydrazo compound contained in the concentrated aqueous solution has the following formula,

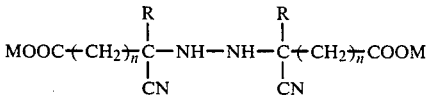

wherein R stands for alkyl of 1 to 6 carbon atoms, M stands for Na or H, and n is an integer of 1 to 6.

13. A process according to claim 1, wherein acetone of below 10° C. is added to the concentrated aqueous solution of a hydrazo compound.

14. A process according to claim 1, wherein chlorine gas is added in an amount of at least 0.5 mole per mole of the keto-acid or its sodium salt.

15. A process according to claim 14, wherein the oxidation is carried out at a temperature lower than 30° C.

16. A process according to claim 13, wherein chlorine gas is added at a temperature of not higher than 10° C.

17. A process according to claim 1, wherein acetone is evaporated from the acetone-water solution containing the diazocyano acid and the diazocyano acid is separated and recovered from the residue.

18. A process according to claim 17, wherein after evaporation of acetone, water is added to the residue in an amount of 100 to 1000 parts by weight per 100 parts by weight of the diazocyano acid.

19. A process according to claim 17, wherein the diazocyano acid is separated and recovered at a temperature lower than 30° C.

20. A process according to claim 1, wherein the diazocyano acid is isolated and purified.

21. A process wherein a diazocyano acid is prepared and isolated according to claim 1 and purified by dissolving the isolated diazocyano acid in a mixed acetone-water solution at a volume ratio of from 75/25 to 95/5, evaporating acetone from the solution and washing the residue with water.

22. A process according to claim 21 wherein the volume ratio of acetone to water is from 75/25 to 90/10.

* * * * *